United States Patent [19]

Schmitt

[11] 4,361,027
[45] Nov. 30, 1982

[54] MEASURING APPARATUS FOR THE QUANTITATIVE DETERMINATION OF A COMPONENT OF A GAS MIXTURE

[76] Inventor: Rudi Schmitt, Karl Kreuter Str. 32, 6700 Ludwigshafen, Fed. Rep. of Germany

[21] Appl. No.: 178,797

[22] Filed: Aug. 18, 1980

[30] Foreign Application Priority Data

Aug. 25, 1979 [DE] Fed. Rep. of Germany ....... 2934426

[51] Int. Cl.³ ............................................. G01N 7/02
[52] U.S. Cl. ..................................... 73/23; 73/863.21; 73/863.81; 73/864.54; 422/88; 374/142
[58] Field of Search .................. 73/864.73, 863.82, 23; 422/88, 89

[56] References Cited

U.S. PATENT DOCUMENTS 3,643,508 2/1972 Schneider ........................ 73/864.73
3,888,123 6/1975 Kuntzinger ...................... 73/863.11

FOREIGN PATENT DOCUMENTS 2603044 8/1977 Fed. Rep. of Germany .
1554068 10/1979 United Kingdom .

Primary Examiner—S. Clement Swisher

[57] ABSTRACT

An improvement in a measuring apparatus for the quantitative determination of a component of a gas sample. The apparatus takes a charge of a predetermined volume of the gas mixture into a metering pump which then pushes it through the absorption unit which adsorbs or absorbs a component of the gas. A probe is used for the intake of the gas and the probe has in the region of its intake opening a thermocouple. In addition, from the cable leading from the thermocouple a reference sensing device such as a second thermocouple is placed in differential connection. A single converter is used for indication of the temperature value and a microcomputer may be used to substantially automate the process.

13 Claims, 6 Drawing Figures

MEASURING APPARATUS FOR THE QUANTITATIVE DETERMINATION OF A COMPONENT OF A GAS MIXTURE

DESCRIPTION

BACKGROUND OF THE INVENTION

The invention concerns a measuring apparatus of the quantitative determination of a component of a gas mixture, consisting of a device for the adsorption of the component, whereby as adsorber is used as the adsorption device, according to published German Application No. 26 03 044 issued to the present inventor, or its corresponding British Pat. No. 1,554,068, both of which are hereby incorporated in this disclosure.

The measuring apparatus according to the above identified patents is suitable, among other things, for the determination of the $CO_2$ content of stack gases. For the establishment and optimization of the degree of effectiveness for a hot system, one should also undertake temperature measurements and measurements of the suction (draft) in the waste gas pipe, whereby the values in the core stream are to be measured, and finally a measurement of the combustion chamber pressure should also be taken.

The measuring apparatus of the invention fulfills these additional missions of indicating directly readable values of the measured result, and also of performing the required calculations.

SUMMARY OF THE INVENTION

The invention makes use of a probe for the intake of gas samples in the region of the intake opening which has a thermocouple and a signal converter for indication or recording of the temperature values. In its thermocouple cable it may have a reference sensing device in differential connection.

It is useful that the probe tube surrounding the thermocouple have radial slits in this region.

According to the preferred model type of the invention, the signal converter is an analog/digital (A/D) converter connected with an amplifier.

In an additional construction of the invention it is proposed that the signal converter is connected, in addition, with the adsorber outlet by a pressure transducer.

It is further proposed that the pressure transducer has another outlet connected by a magnetic valve with the atmosphere, to which the gas duct of the probe is suitable to be connected. The transducer is preferably a piezoelectric silicon crystal transducer which in any case is connected in series with a pressure reducing volume.

The signal converter may be connected at the output end with memory storage. The microcomputer can also be connected with a basic value recall, or also with a data printer.

A further feature of the invention is that the probe may have a hollow handle with a condensate separator in it.

For the exact adjustment of the probe, a probe holder is provided which is constructed as a frame with a tension spring and a swingable and lockable holding element with a drilled hole for the probe, and can have a notch for the probe.

BRIEF DESCRIPTION OF THE DRAWINGS

The invention is explained in detail by means of the drawings. They show.

DESCRIPTION OF PREFERRED EMBODIMENT

Figure 1:
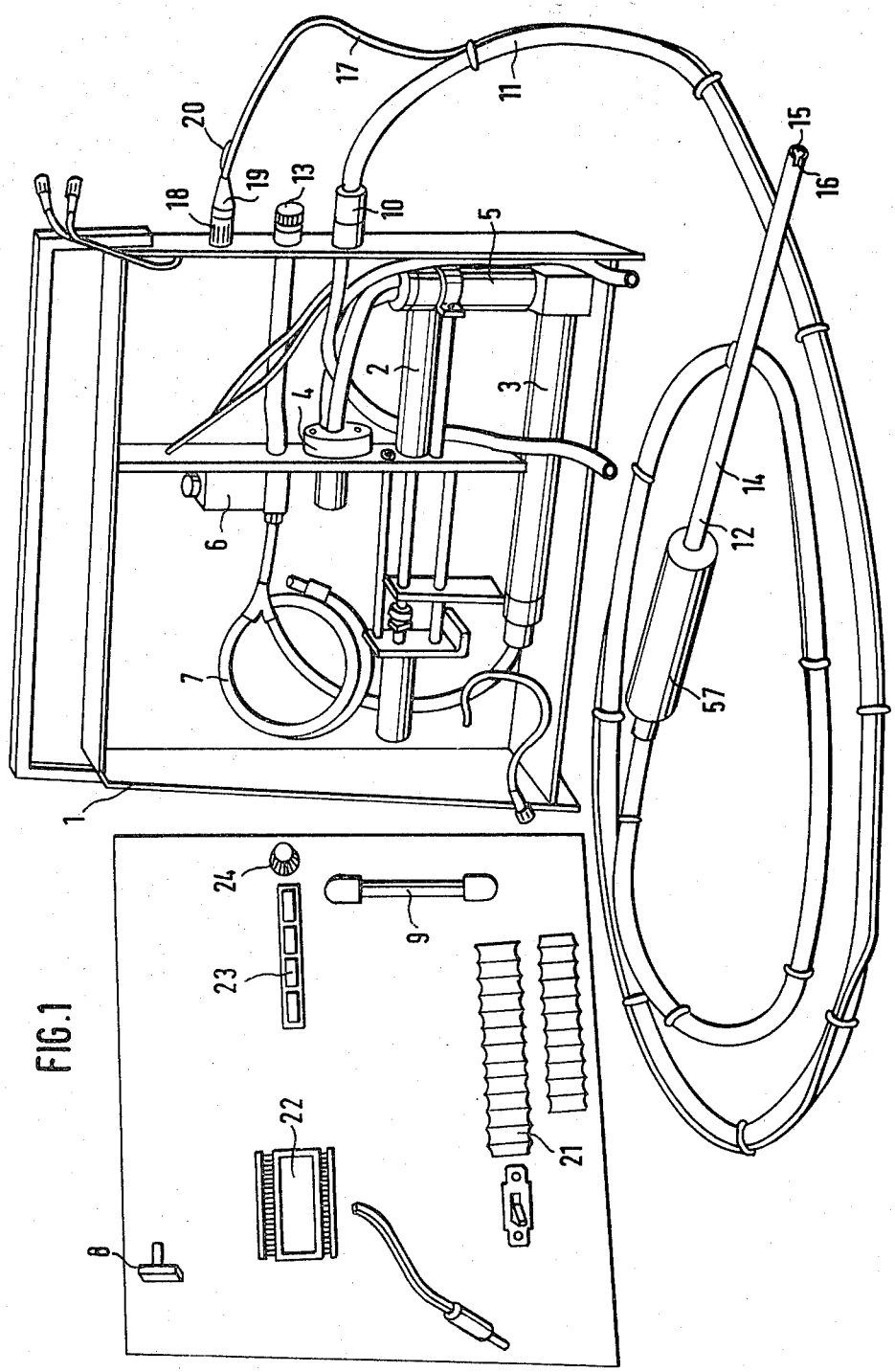
FIG. 1 is a view of a measuring apparatus embodying the invention without the front plate, with a view into the housing with the main parts arranged in it, and of other parts on a mounting plate.
Figure 2:
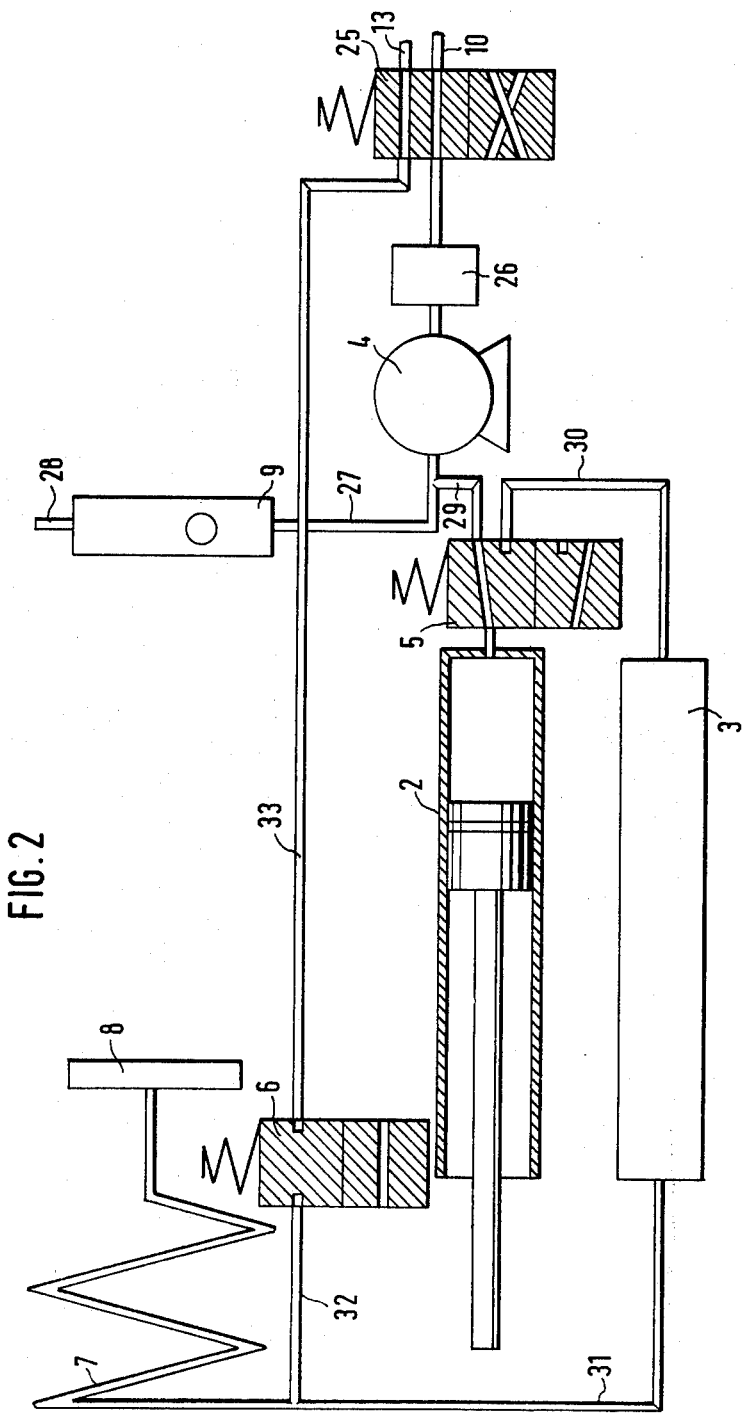
FIG. 2 is a connection diagram of the mechanical parts of the measuring apparatus.
Figure 3:
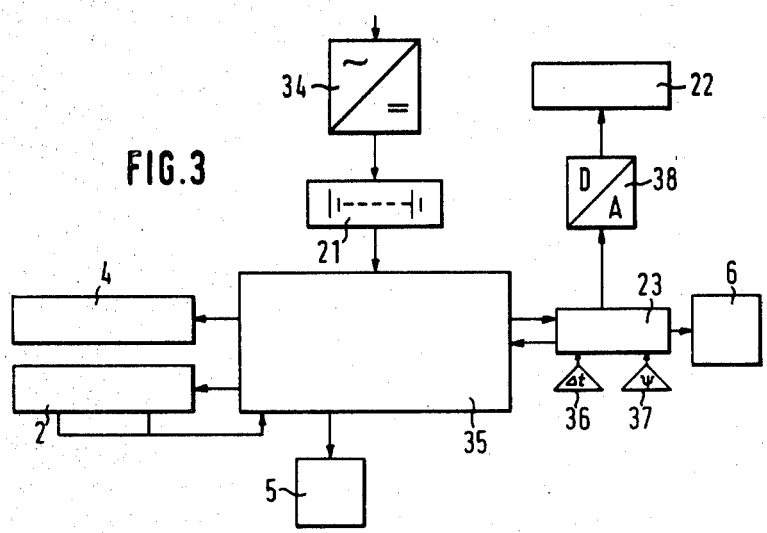
FIG. 3 is a block diagram of the measuring apparatus.

The measuring apparatus consists of the housing 1 with the arranged therein piston metering pump 2, an adsorber 3, a gas conveying pump 4, magnetic valves 5 and 6, a pressure reducing volume 7, a pressure transducer 8, and a flow monitor 9, which are connected with each other by hose ducts.

Although the measuring apparatus described utilizes an adsorption unit, it will be appreciated that in some cases it may be advisable to use an absorption unit instead. Consequently, the term "adsorption unit" as used in the specification should be taken to include such an absorption unit. As a rule, an adsorption unit is to be preferred since an apparatus operating with solid substances is obviously immune to tilting and consequently more sturdy as far as handling is concerned. Moreover, there are more possibilities of gas analysis when using an adsorption unit. A precondition for the use of an adsorption unit is, however, the use of a sufficiently powerful metering pump which is capable of forcing the gas sample through the adsorption unit.

Furthermore, the apparatus has a gas inlet 10, to which the duct 11 from the probe is connected. Alternatively, the duct 11 can be connected to the gas inlet 13. The probe tube 14 has at its end a central opening 15 and radial slits 16. In the opening 15 a thermocouple 17' is centrally arranged, whose lead 17 is connected to the input 18 of the measuring apparatus. Another thermocouple 20 is connected in differential connection in the lead 17, in the region of the plug 19.

Figure 6:
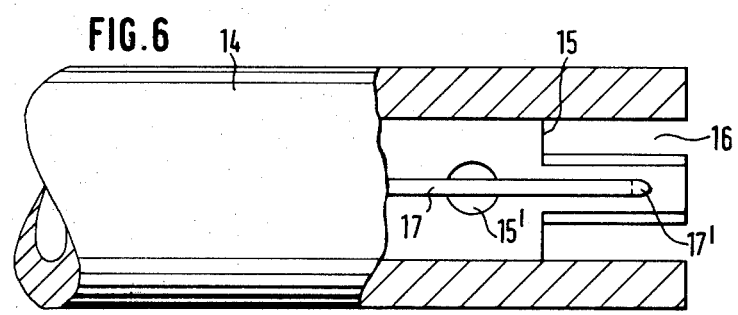
FIG. 6 is a partial cut away of a probe head.

The probe head itself is presented in FIG. 6. Behind the central opening 15, an additional intake opening 15' can be provided.

The measuring apparatus is operated by a battery 21 and has a digital indicator 22, as well as a controller 23 for the recall of individual functions. Furthermore, a zero adjustment 24 is provided.

At the gas inlets 10 and 13, a magnetic valve 25 can be connected, so that the alternative connecting of duct 11 to one of the two inlets can be omitted. The inlet 10 is furthermore connected through a filter 26 with the gas conveying pump 4, which conveys the gas from the stack through a duct 27 and a flow monitor 9 to the outlet 28.

A branch tube 29 is connected to the duct 27, which is connected through the magnetic valve 5 with the piston pump 2 by a duct 30 with the adsorber 3. The adsorber outlet is connected by a duct 31 and the pressure reducing volume 7 to the piezoelectric silicon crystal transducer 8. Furthermore, to the tube 31 is connected a branch tube 32 which is connected through the magnetic valve 6 and a duct 33 with the magnetic valve 25 and the outlet 13. By manipulation of the valve 25, the duct 33 is connected with either the outlet 10 or the outlet 13 and the filter 26 is connected with the outlet (10,13) to which duct 33 is not connected.

Figure 4:
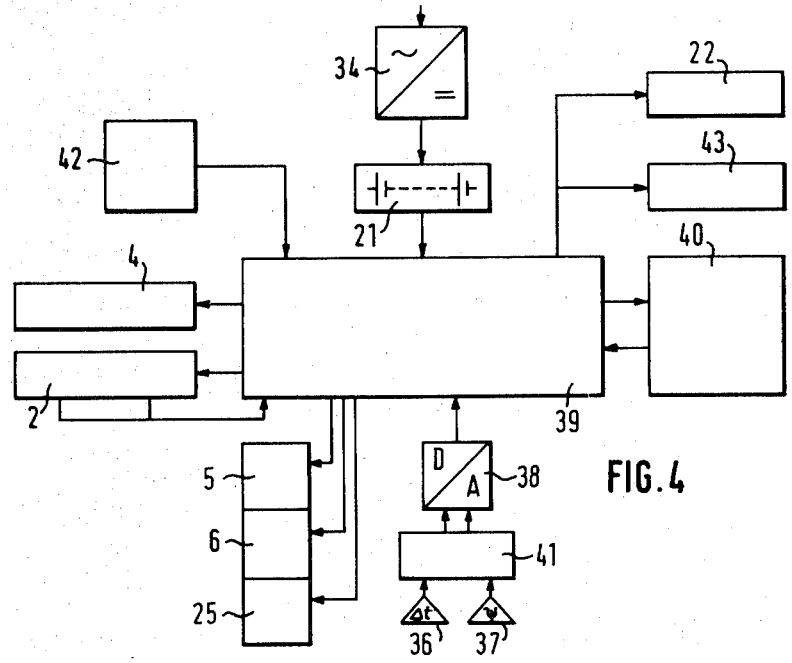
FIG. 4 is a modified block diagram.
Figure 5:
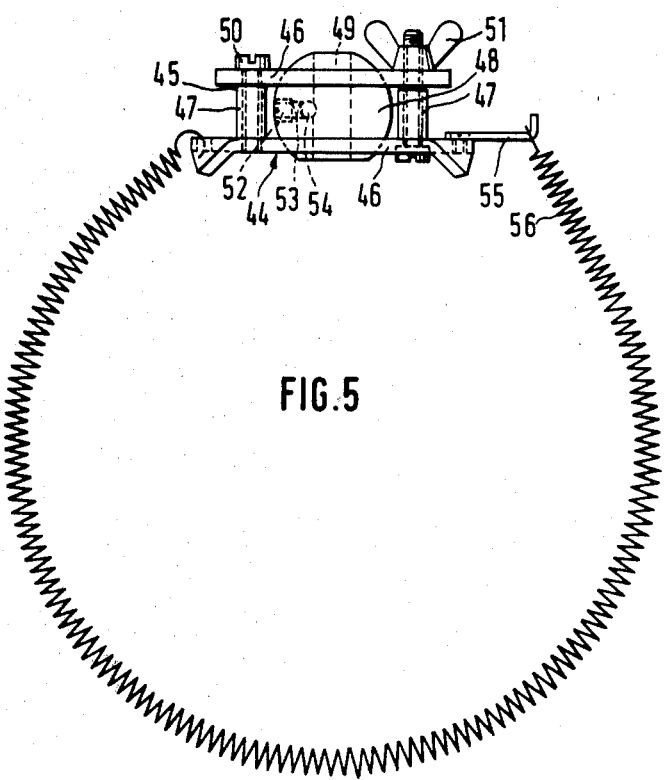
FIG. 5 is a probe holder.

Furthermore, the measuring apparatus has a charging apparatus with which the battery 21 can be charged. The battery is connected with a control part 35, which in turn is connected with the piston pump 2 and its control element, e.g. limit switches for the two extreme pump (piston) positions. Further connections exist with the gas conveying pump 4, the magnetic valve 5, as well as the controller 23, through which the temperature signal 36 and the pressure signal 37 are recallable. These signals are amplified by an amplifier integrated in the control part 35 and given by the controller 23 to an analog-digital converter 38 which is connected with the digital indicator 22. The magnetic valve 6 is operable through the controller 23. If a magnetic valve 25 is provided, then an additional button can be provided in controller 23 for its manipulation. Furthermore, the zero adjuster 24 belongs to the controller 23, which can be operated after switching valve 6 on. In the alternative embodiment shown in FIG. 4, the battery 21 is connected with a microcomputer 39 and a memory storage 40, and to the piston pump 2 and the gas conveying pump 4 in an analogous manner. The signals 36 and 37 arrive, after amplification by the amplifier 41, through the A/D converter into the microcomputer 39. This has an additional input for a basic value 42, as well as outputs for the magnetic valves 5, 6 and 25, as well as for the digital indicator 22 and a printer 43 connected in parallel with it.

The probe holder 44 has a frame 45, consisting of an upper and a lower plate 46 which are connected by lateral crossbeams 47. Parallel to the crossbeams 47, a central block is arranged which has a laterally drilled hole 49 in the block 48, whose size corresponds to that of the probe tube 14. The block 48 is held by screws 50 and wing nut 51. At right angles to the laterally drilled hole 49 in the block 48 is a tapped drilled hole closed by a set screw 52, in which a spring 53 and a ball 54 are arranged. On one of the crossbeams a hook 55 is arranged on which a tension spring 56 is hangable, whose other end is fastened to the opposite lying crossbeam.

In the probe handle is placed a condensate separator which, can consist of metal wool, and over which the gas to be analyzed is dried.

The measuring apparatus operates in the following way. After opening a bore hole in the stack gas pipe, the spring 56 of the probe holder is laid around the stack gas pipe and fastened to the frame 45 so that the probe tube 14 of the probe 12 of the measuring apparatus can be introduced. After preparation of the zero adjustment for pressure with the push button concerned on the controller 23, as well as manipulation of the temperature push button of the controller 23, the probe can be pushed through the cross section of the stack gas pipe and can also be swung around until the highest temperature indication is reached, i.e. the probe tube is introduced into the core stream of the waste gas. By tightening the wing nut 51, it is assured that the probe does not shift during the measuring process. The gas then flows through the probe and through duct 11 into gas inlet 10. From there it passes through the gas conveying pump 4 and out of the apparatus through outlet 28.

When a measurement is desired, metering piston 2 is activated to draw in through valve 5 charges of the gas to be measured. The pump cycle is repeated several times to insure the gas within the pump chamber corresponds with the gas to be measured, and when this has been done the piston pump takes a charge of a predetermined volume of gas into its chamber by reaching its furthest withdrawn position. Switch 5 is changed so to connect the pump with duct 30 and the piston pushes the charge through the adsorber 3 and into the pressure reducing volume 7. The suction stroke of the piston pump 2 is now undertaken pulling the sample back into its chamber. However, adsorption will have taken place and consequently a subatmospheric pressure is produced in the air space of the system which may be measured by pressure reducing volume 7 and pressure transducer 8. This pressure corresponds to the adsorbed portion of the gas sample which allows for analysis of the components such as $CO_2$. The basic use of the piston pump is explained in more detail in the above identified foreign patents issued to this inventor.

Subsequently, the program for $CO_2$ measurement can be recalled by appropriate button pressing on the controller 23, whereby the control part 35 or the microcomputer 39 operates the piston pump 4 at least once in the no-load stroke, and subsequently one or more gas samples are pushed through the adsorber 2. The partial vacuum formed by the adsorption appears on the digital indicator 22.

After changing over or switching the gas duct of the probe 12 to the inlet 13, the measurement of the pressure can be undertaken by button pressing again on the controller 23. Finally by changing the probe over into the combustion chamber where the gas is produced, the combustion chamber pressure can also be measured.

The apparatus can be further modified by addition of a microcomputer so that after setting up the probe, the entire measuring process, with the exception of the pressure measurement in the combustion chamber, proceeds automatically, and the measured values are stored. After changing over the probe to the combustion chamber, the measured values are also received by the microcomputer with recall of the given basic values, evaluated, and the final result is printed out.

After completion of the measurements, the probe 12 is fastened in a vertical position on the measuring apparatus, so that the deposited moisture present in the condensate separator can drip out through the intake opening 15.

According to another embodiment a resistance thermometer is used instead of the thermocouple 17', connected directly by lead 17 to the input 18 of the measuring apparatus. The resistance thermometer can be arranged projecting before the opening 15 of the probe tube 14. Because of the greater accuracy of the resistance thermometer the radial slits 16 at the intake end of probe tube 14 can be omitted.

I claim:

1. An improved measuring apparatus for the quantitative determination of a component of a gas mixture of the type having a sorption unit containing material which sorbs said component, a metering pump for forcing a predetermined volume of the gas mixture through the sorption unit, the gas mixture being drawn into the metering pump by a probe which opens into the gas mixture for intake of said predetermined volume and a device for measuring a parameter of the gas which emerges from the sorption unit, the improvement characterized by the probe having a thermocouple in the region of the intake opening and a reference sensing device in a cable from the thermocouple in differential connection, and further comprising a signal converter for indication of the temperature values.

2. The measuring apparatus of claim 1, wherein the thermocouple is surrounded by a probe tube which has radial slits near the thermocouple for intake of the gas sample.

3. The improved measuring apparatus of claim 1, wherein the signal converter comprises an analog to digital converter connected with an amplifier.

4. The improved apparatus of claim 3, wherein the signal converter is additionally connected with an outlet from the adsorption unit by a pressure transducer.

5. The apparatus according to claim 4, wherein the pressure transducer has an additional outlet connecting with the atmosphere through a magnetic valve alternatively connectable with a gas duct from the probe.

6. The apparatus of claim 5, wherein the pressure transducer is a piezoelectric silicon crystal transducer.

7. The apparatus of claim 6, wherein the pressure transducer is connected in series with a pressure reducing volume.

8. The apparatus of claims 3, 4 or 7, wherein the signal converter is connected at its output end to a microcomputer consisting of a microprocessor and a memory.

9. The apparatus of claim 8, wherein the microcomputer is connected with a basic value recall.

10. The apparatus of claim 9, wherein the microcomputer is connected with a data printer.

11. The apparatus according to claim 1 or 7, wherein the probe has a hollow handle with a condensate separator arranged therein.

12. The apparatus according to claim 11, further comprising a probe holder comprising means for attachment of the holder to a container containing the gas to be sampled, a swingable holding element for locking the probe in the holder.

13. The apparatus of claim 12, wherein the holding element comprises a pair of spaced apart frame plates through which the frame passes joined by cross members, one of which is controlled by a screen for swinging one of said plates relative the other.

* * * * *